(12) United States Patent
Aux Epaules et al.

(10) Patent No.: US 8,894,660 B2
(45) Date of Patent: Nov. 25, 2014

(54) ACETABULAR CUP INSERTER AND IMPACTOR

(75) Inventors: Arnaud Aux Epaules, Saint Aubin sur Mer (FR); Antoine Coustance, Hérouville St Clair (FR)

(73) Assignee: Stryker Ireland Limited (IE)

( * ) Notice: Subject to any disclaimer, the term of this patent is extended or adjusted under 35 U.S.C. 154(b) by 383 days.

(21) Appl. No.: 13/302,438

(22) Filed: Nov. 22, 2011

(65) Prior Publication Data

US 2012/0136361 A1 May 31, 2012

(30) Foreign Application Priority Data

Nov. 25, 2010 (GB) .................................. 1020040.0

(51) Int. Cl.
*A61B 17/56* (2006.01)
*A61F 2/46* (2006.01)
*A61F 2/30* (2006.01)

(52) U.S. Cl.
CPC ....... *A61F 2/4609* (2013.01); *A61F 2002/4623* (2013.01); *A61F 2002/4627* (2013.01); *A61F 2002/4681* (2013.01); *A61F 2002/4628* (2013.01); *A61F 2002/30579* (2013.01); *A61F 2002/30471* (2013.01)
USPC ........................................................ 606/91

(58) Field of Classification Search
CPC ......... A61B 17/56; A61B 17/88; A61B 17/92
USPC ............ 606/86 R, 88–91, 99, 100; 623/22.12
See application file for complete search history.

(56) References Cited

U.S. PATENT DOCUMENTS

| | | | | |
|---|---|---|---|---|
| 5,928,287 A * | 7/1999 | Keller | ........................ | 623/22.21 |
| 5,954,727 A * | 9/1999 | Collazo | ........................... | 606/91 |
| 7,341,593 B2 | 3/2008 | Auxepaules et al. | | |
| 7,462,180 B2 | 12/2008 | Raugel et al. | | |
| 7,682,363 B2 * | 3/2010 | Burgi et al. | ..................... | 606/91 |
| 7,833,276 B2 | 11/2010 | Auxepaules et al. | | |
| 7,993,348 B2 | 8/2011 | Conte et al. | | |
| 8,142,439 B2 * | 3/2012 | Parker | ............................ | 606/91 |
| 2002/0177854 A1 | 11/2002 | Tuke et al. | | |
| 2008/0021481 A1 | 1/2008 | Burgi | | |
| 2011/0130763 A1 | 6/2011 | Aux Epaules et al. | | |
| 2011/0184423 A1 | 7/2011 | Rushton et al. | | |

FOREIGN PATENT DOCUMENTS

EP 1570815 A1 9/2005
FR 2663840 A1 1/1992

OTHER PUBLICATIONS

Extended European Search Report for Application No. 11250901 dated Mar. 13, 2012.

* cited by examiner

*Primary Examiner* — Christopher Beccia
(74) *Attorney, Agent, or Firm* — Lerner, David, Littenberg, Krumholz & Mentlik, LLP

(57) ABSTRACT

A prosthetic acetabular cup inserter and impactor has a body, a cup engaging element disposed at a first end of the body which is adapted to engage an inner surface of a cup with which it is used. An operating system is adapted to axially rotate the cup engaging element in relation to the body in use. An impaction plate that is adapted to engage an undulating rim of the cup is disposed between the body and the cup engaging element. The impaction plate is connected to the operating system by a linkage which acts to axially rotate the impaction plate in unison with the cup engaging element in use.

24 Claims, 5 Drawing Sheets

ACETABULAR CUP INSERTER AND IMPACTOR

CROSS-REFERENCE TO RELATED APPLICATION

The present application claims priority from Great Britain Patent Application No. 1020040.0 filed Nov. 25, 2010, the disclosure of which is hereby incorporated herein by reference.

BACKGROUND OF THE INVENTION

The present invention relates to a prosthetic acetabular cup inserter and impactor, for use particularly, but not exclusively, in minimal invasive surgery (MIS) with a short incision.

Prosthetic acetabular cup inserter and impactors are used to implant prosthetic acetabular cups into the cavity of a patient's hip, and generally comprise an elongate straight or curved body with a cup engaging head at a first end thereof, and a handle and impaction anvil at a second end thereof. The surgeon releasably fits a cup implant to the cup engaging head, and then positions the cup inside the patient's hip. He then applies a hammering force to the impaction anvil to secure the cup in place, before releasing the cup from the cup engaging head.

In Minimally Invasive Surgery (MIS) it is common to use an inserter and impactor with a curved body, which is shaped to minimise trauma to the patient when it is inserted. In many cases the cups have irregular shapes and/or holes which have to be aligned inside the patient at a particular angle. With such constructions it is important to axially align the cup correctly in relation to the body of the inserter and impactor prior to insertion, so it is properly aligned with the patient's hip when the curved body is inserted as desired.

In U.S. Patent Application Publication No. 2011/0130763 in the name of the applicant, the disclosure of which is incorporated herein by reference, a prosthetic acetabular cup inserter and impactor is disclosed in which the cup engaging means can be axially rotated in relation to the body. In particular, there is a locking means which locks the cup engaging means against axial rotation, which can be released to allow it to be axially rotated in relation to the curved body, and then re-locked when a desired angular position is achieved. Thus, a surgeon can position the cup in relation to the curved body to his liking prior to, or even during, insertion.

However, in this construction the cup engaging means and the body can only be rotated in relation to one another by direct manipulation thereof (or when the cup is held in position inside the acetabulum of the patient). There is shown an operating knob which can rotate a part of the cup engaging means, but this is only for the purposes of engaging and disengaging the cup.

Other devices owned by the assignee or its affiliates of the present invention are U.S. Pat. Nos. 7,341,593, 7,462,180 and 7,993,348, U.S. Patent Application Publication Nos. 2011/0130763 and 2011/0184423.

In U.S. Patent Application Publication No. 2008/0021481, in the name of BURGI, there is disclosed a prosthetic acetabular cup inserter and impactor in which the cup engaging means can be axially rotated in relation to the body by an operating means. The operating means comprises a rigid drive train fitted inside the curved body, which has a rotation handle at one end. The cup is screw threaded to the opposite end of the drive train, and initially the drive train is axially rotated by the handle to facilitate this. However, once this is achieved the surgeon may then axially rotate the handle to orient the cup to a preferred position. The cup is then drawn back onto a head to lock it in position. To release the cup engaging means from the cup after insertion, the handle is axially rotated in the opposite direction to as initially in order to release the screw threaded connection.

However, the device shown in BURGI finds limited application, as it can only be used in instances where a cup is engaged via a screw threaded hole formed in its inner surface. In particular, it cannot function with a cup which is not provided with such a hole, which may be preferred. In addition, some cups are not only engaged by an inserter and impactor at their inner surface, but also by an impaction plate applied to their outer rim. BURGI can only be used to rotate a cup engaging means engaging a cup at its inner surface, and not where a cup is also engaged at its outer rim, as there is no way to also rotate an impaction plate.

In U.S. Pat. No. 7,833,276, assigned to the assignee of the present application there is disclosed a prosthetic acetabular cup comprising an inner part-spherical bearing surface and an outer peripheral rim portion which is shaped to mimic the contours of the natural shape of an acetabulum. The outer peripheral rim portion has an illium rim portion, an ischium rim portion and a pubis rim portion. The portions of the rim between the pubis rim portion and the illium rim portion and between the pubis rim portion and the ischium rim portion are concave and slightly more proximal than the pubis rim portion; the portions of the rim between the illium rim portion and the pubis rim portion, and between the illium rim portion and the ischium rim portion are more concave and proximal than the illium rim portion; and the portions of the rim between the ischium rim portion and the illium rim portion and between the ischium rim portion and the pubis rim portion are more concave and proximal than the ischium rim portion.

This document also discloses a prosthetic acetabular cup inserter and impactor for use with such an acetabular cup, which comprises an annular disc with an annular engagement wall which is shaped to engage the outer peripheral rim of the cup. The annular engagement wall is fixed in relation to the body of the inserter and impactor. With this type of cup and inserter and impactor it is not possible to axially rotate the cup in relation to the engagement wall, as they have irregular shapes. Therefore, axial rotation of the cup in relation to the body in this case is not possible.

In U.S. Patent Application Publication No. 2011/0130763 referred to above, and in U.S. Pat. No. 7,341,593, the disclosures of which are incorporated herein by reference, both assigned to the assignee of the present invention, there are disclosed prosthetic acetabular inserter and impactors which engage the interior surface of the cup by means of a compressible or expandable resilient ring. This is advantageous because no fixing means are required on the interior surface of the cup. However, in U.S. Patent Application Publication No. 2011/0130763 there is no impaction plate, and although there is such a feature in U.S. Pat. No. 7,341,593 there is no relative axial rotation at all in that case.

The present invention is intended to overcome some of the above problems.

BRIEF SUMMARY OF THE INVENTION

Therefore, according to the present invention a prosthetic acetabular cup inserter and impactor comprises a body, a cup engaging element disposed at a first end of the body and adapted to engage an inner surface of a cup with which it is used. Operating elements are provided which are adapted to axially rotate the cup engaging element in relation to the body in use, in which an impaction plate adapted to engage a rim of the cup is disposed between the body and the cup engaging element, and in which the impaction plate is connected to the operating elements by a linkage which acts to axially rotate the impaction plate in unison with the cup engaging element in use.

Thus, the present invention provides an inserter and impactor with the advantageous relative axial rotation between the cup engaging element and the body, which can be used with cups with an irregularly shaped outer peripheral rim portion acted upon in use by a correspondingly shaped impaction plate, because the impaction plate can also be rotated.

The linkage can be a direct connection between the operating means and the impaction plate, however such a configuration would require either the impaction plate and the cup engaging element to be unitary, or for there to be separate connections between the operating elements and the cup engaging element and between the operating elements and the impaction plate. If the cup engaging element and the impaction plate were unitary it would prevent the inter changing of these parts, which could be a disadvantage, and if there had to be two connections between the operating elements and the cup engaging element and between the operating elements and the impaction plate, there would be a proliferation of parts, and the possibility of non-synchronous axial rotation.

Therefore, in a preferred construction the linkage can comprise an axial rotational connection between the cup engaging element and the impaction plate. As such, the impaction plate is rotated by virtue of the rotation applied to the cup engaging element.

The cup engaging element can be any of the known constructions, including a screw thread fixing, or by means of a compressible or expandable resilient ring. However, preferably the cup engaging element can comprise a cup engaging element adapted to engage an inner surface of the cup via outward biasing thereof, and a biasing element adapted to bias the engaging element outwardly via relative axial movement therewith. In basic terms this is like the cup engaging element in U.S. Pat. No. 7,341,593, referred to above.

The term "biasing" is used here because the invention includes cup engaging elements which outwardly expand to engage a cup, as well as those which fit snugly inside a cup and then engage it by being compressed into greater contact therewith, or a mixture of both.

In a preferred construction the operating elements can be adapted to axially move the biasing means from a preliminary position in which the cup is partially engaged with the cup engaging element, into an engaged position in which the cup is fully engaged with the cup engaging element. This is somewhat different than the construction shown in U.S. Pat. No. 7,341,593, and allows for the cup to be held on the cup engaging element in a partially engaged manner while it is axially rotated, and to then be held firmly once it is in the correct position. In such a construction the cup engaging element is compressed into greater contact with the cup to engage it fully, rather than physically expanding outwardly, although there may be a degree of this in practice. This axial movement of the biasing element to fully engage the cup is a separate action from the axial rotation of the cup engaging element.

A locking element can be provided between the body and the cup engaging element which can be movable between a locked position in which the cup engaging element is locked against rotation in relation to the body, and an unlocked position in which the cup engaging element is rotatable in relation to the body.

The operation of the operating elements which serves to move the biasing element into said engaged position can also serve to move the locking element into the locked position, and an operation of the operating element which serves to allow for the biasing element to move into the preliminary position can also serve to allow for the locking element to move into the unlocked position.

Therefore, with the cup partially engaged on the cup engaging element it can be axially rotated in relation to the body because the locking element is in the unlocked position, and when the cup is in the correct position it can be fully engaged on the cup engaging element and locked against axial rotation with a single movement of the biasing element.

Preferably the locking element can be spring loaded into the unlocked position. This removes the requirement for the operator to hold the cup engaging element in the unlocked position, so it can be more readily rotated.

The locking element can comprise co-operating sets of teeth provided at the first end of the body and at a rear face of the impaction plate.

In one construction the impaction plate can comprise a front face with an annular cup engaging wall. The cup engaging element can abut against the front face, and the biasing element can move towards the front face when it is moved into the engaged position.

The cup engaging element can comprise a resilient ring comprising a central aperture which tapers in a direction toward the front face, and the biasing element can comprise a cone element disposed within the aperture, which comprises a taper corresponding with that of said aperture. Therefore, axial movement of the cone element inside the resilient ring causes it to expand and engage the cup and/or be compressed into greater contact therewith.

This is an expedient configuration for converting the axial movement of the cone element into the radial biasing of the resilient ring in order to engage the cup, but it presents a difficulty when trying to impart to the impaction plate the separate axial rotation of the cup engaging means relative to the body prior to full engagement of the cup, because the cone element is disposed inside the resilient ring.

Therefore, in a preferred construction the axial rotational connection between the cup engaging element and the impaction plate can comprise a first radially outwardly extending spigot provided on the cone element which axially rotationally engages a radially extending slot provided in the resilient ring at a first position, and a second radially inwardly extending spigot provided on the cup engaging wall which axially rotationally engages the radially extending slot at a second position. This is an expedient construction which ensures that axial rotation of the biasing element is transmitted to the cup engaging element and then the impaction plate in a regular, synchronous manner. The use of such a slot also facilitates the axial relative movement between the biasing means and the cup engaging element without the radial connection therebetween causing any difficulty. The slot also advantageously allows for the resilient ring to be radially outwardly biased and/or expanded in use.

Preferably the operating elements can comprise a rigid drive train carried by the body, which can comprise a connection to the biasing element at a first end thereof, and an operating knob at a second end thereof, which operating knob can be axially rotatable to rotate the biasing element in relation to the body, and separately operable to axially move the biasing element from the preliminary position into the engaged position. Such rigid drive trains are known, but they have never had this particular type of dual purpose.

The operating knob can be operable to axially move the biasing element in any know way, for example if the rigid drive train is linear in nature, it can simply be axially moved back and forth. However, as referred to below, the body is preferably curved, so the rigid drive train can follow this curved shape. Therefore, second end of the rigid drive train can be carried on a rack, which can be disposed in a slot in the body, and be moveable therethrough both towards and away from the body. The position of the rack can be determined by a spring loaded ratchet disposed inside the body, and which can extend laterally into the slot to engage the rack. This ratchet can be movable between an engaged position and a disengaged position. In the engaged position the ratchet can allow the rack to ride over it when the rack is moved towards the body, and it can prevent the rack from moving away from the body. In the disengaged position the ratchet can allow the rack to move freely in the slot. The movement of the second end of the rigid drive train towards the body can be converted by the rigid drive train into axial movement of the biasing element into the engaged position.

In order to facilitate the above described conversion, the rigid drive train can comprise an outer end rod, an intermediary rod and an inner end rod, connected together end to end in sequence by universal joints. The outer end rod can be mounted part way along its length in a first pivot mounting, the intermediary rod can be mounted part way along its length in a second pivot mounting, and the inner rod can be mounted for axial movement in a sleeve mounted at a first end of the body. Therefore, movement of the second end of the rigid drive train towards the body can rotate the outer end rod lengthwise about the first pivot mounting in a first direction, rotate the intermediary rod lengthwise about the second pivot mounting in a second direction, and move the inner rod substantially axially through the sleeve.

It will be appreciated that the lengthwise rotation of intermediary rod may not be transmitted into a perfectly linear axial movement of inner end rod, because the universal joint therebetween follows an orbital path about the second pivot mounting. However, the required axial movement of the inner end rod is short, and any deviation caused by the orbital movement of this universal joint is well within functional tolerances.

In one construction the biasing element can be releasably fixed to the first end of the drive train with a screw thread. Alternatively, the biasing element can be releasably fixed to the first end of the drive train with a spring loaded quick release mechanism. Either of these arrangements is acceptable, but the latter allows for the inserter and impactor to be more readily dismantled.

In one version of the invention a sleeve can be disposed between a first end of the body and the impaction plate; the impaction plate can comprise a central aperture through which the sleeve passes; the impaction plate can be axially moveable on the sleeve between the locked and unlocked positions of the locking element; and a second end of the sleeve can be snap-fitted to the first end of the body. This construction readily facilitates the small movements of the impaction plate in use with the minimum number of parts.

As an alternative to the above, the impaction plate can be mounted to the first end of the body with a spring loaded quick release mechanism. This would allow for the inserter and impactor to be more readily dismantled. In one embodiment the impaction plate can be freely mounted on said sleeve, and be retained thereon by the cup engaging element abutting against the front face thereof. With this construction the spring loaded quick release mechanism which serves to mount the impaction plate to the first end of the body can be the same mechanism which releasably fixes the biasing element to the first end of the drive train.

The cup engaging element can be a snap-fit onto the front face of the impaction plate. For example, it could be slightly larger than the inner diameter of the cup engaging wall, so it is retained within it. As an alternative, the cup engaging element can be disposed against the front face without constraint. This is possible because it can be held against the front face by the biasing element inside it.

A second end of the body can be provided with a handle and an impaction plate or anvil. The handle facilitates the manipulation of the inserter and impactor in use, and the impaction anvil allows for an impaction force to be imparted to the cup to fit it in the acetabulum in use.

As mentioned above, the body can be curved, in the known way which is suitable for MIS. If this is the case, longitudinal axes of the cup engaging element and the handle can be substantially aligned. This is a known configuration, and allows the impaction force to be applied to the cup in a linear fashion.

As described above, the present invention finds particular application with cups with an irregularly shaped outer peripheral rim. Therefore, preferably the annular cup engaging wall can comprise an irregular upper surface comprising a plurality of convex portions.

Other aspects of the invention are described in an application filed on the same day as the present application entitled "Prosthetic Acetabular Cup Inserter And Impactor" assigned to the assignee of the present application.

BRIEF DESCRIPTION OF THE DRAWINGS

The present invention can be performed in various ways, but one embodiment will now be described by way of example, in which.

DETAILED DESCRIPTION

Figure 1:
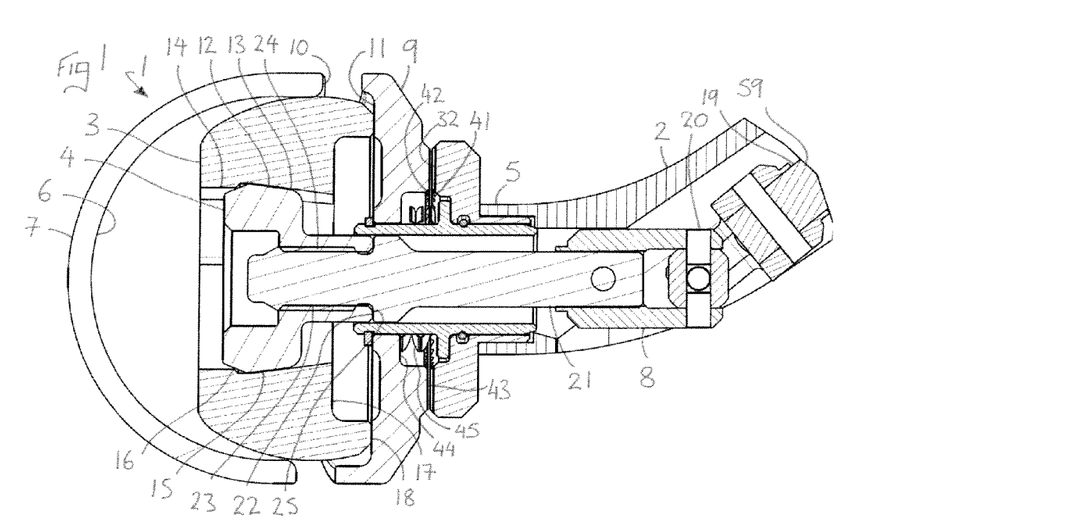
FIG. 1 is a cross-sectional side view of a portion of a prosthetic acetabular cup inserter and impactor according to the present invention, in a first in use configuration.

Therefore, as shown in FIG. 1, a prosthetic acetabular cup inserter and impactor (a leading portion of which 1 is shown in FIG. 1) comprises a body 2, a cup engaging element, in the form of resilient ring 3 and cone element 4, disposed at a first end 5 of said body 2 and adapted to engage an inner surface 6 of a cup 7 with which it is used, and operating elements, in the form of rigid drive train 8, adapted to axially rotate cup elements (3, 4) in relation to body 2 in use. An impaction plate 9 adapted to engage a rim 10 of cup 7 is disposed between body 2 and said cup engaging element (3, 4). As described further below, impaction plate 9 is connected to operating elements (3, 4) by a linkage which acts to axially rotate said impaction plate 9 in unison with the cup engaging element (3, 4) in use.

As described above, the cup engaging element comprises deformable resilient ring 3, which can engage inner surface 6 of cup 7 via outward biasing and/or expansion thereof. The ring 3 rests against a front face 11 of impaction plate 9, and comprises a central aperture 12 which tapers in a direction towards front face 11. As is clear from FIG. 1, the cone element 4 is disposed within aperture 12, and comprises a taper corresponding with that of aperture 12. Therefore, relative axial movement of the cone element 4 towards front face 11 in use causes the ring 3 to be radially outwardly biased and/or expanded to engage the cup 7.

The central aperture 12 comprises a first portion 13 which comprises the above described taper, and a second narrower portion 14 above first portion 13. The cone element 4 comprises a first portion 15 which comprises the above described taper, and a second portion 16 above first portion 15, which tapers in the opposite direction. The second portion 14 of the aperture 12 serves to retain the cone element 4 therein. It may also prevent the ring 3 from moving axially towards front face 11 of the impaction plate 9 when the cup 7 is initially applied to the ring 4 in use, as described further below. The second portion 14 of the aperture 12 engages the second portion 16 of the cone element 4, and significant axial compression of the resilient ring 3 is prevented. The second portion 14 of the aperture 12 also assists in the dismantling of the cone element 4 and the resilient ring 3. When the cone element 4 is removed from the aperture 12, the second portion 16 of the cone element 4 engages the second portion 14 of the aperture 12 and forces the resilient ring 3 to expand, allowing the cone 4 to be freed.

The resilient ring 3 also comprises a recess 17 on an underside 18 thereof, which provides space for other components, as described further below.

The rigid drive train 8 comprises a number of rods 19, held together with universal joints 20. An inner end rod 21 comprises a collar 22 and a screw threaded portion 23. The cone element 4 comprises a corresponding central aperture 24 provided with a screw thread, which is screwed onto to said screw threaded portion 23, such that an underside 25 of the cone element 4 abuts against collar 22.

Figure 2:
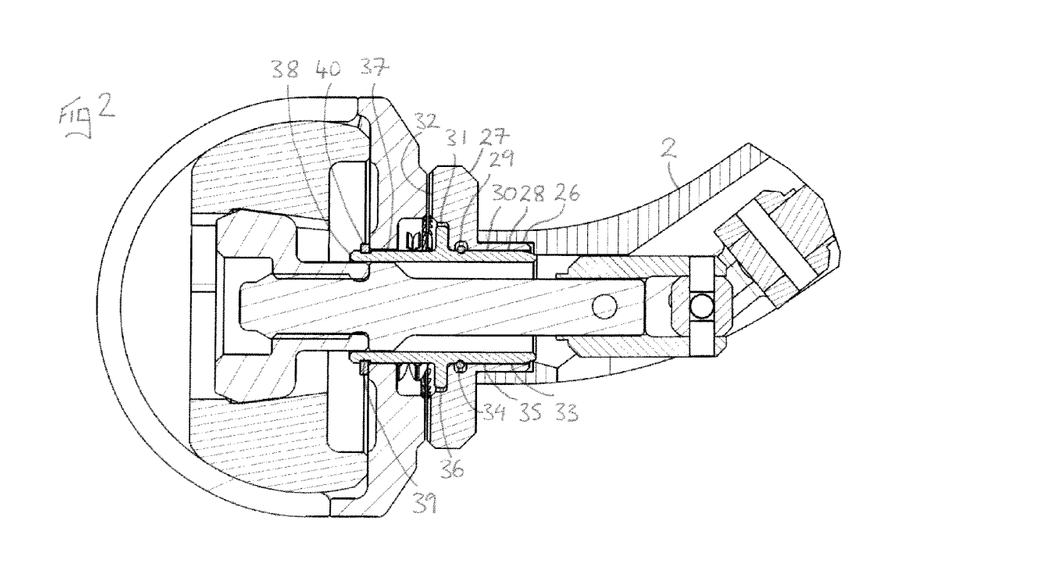
FIG. 2 is a cross-sectional side view of the portion of the prosthetic acetabular cup inserter and impactor as shown in FIG. 1, in a second in use configuration.

Referring now to FIG. 2, the first end 5 of body 2 is provided with a recess 26, in which is mounted a collar component 27. The collar component 27 has a central aperture 28, an annular trough 29 provided on an inner surface 30 of the central aperture 28, and an annular recess 31 in a front face 32 thereof.

Mounted in central aperture 28 of the collar component 27 is sleeve 33. In particular, the sleeve 33 has a resilient ring 34 mounted to an outer surface 35 thereof which is a snap-fit in annular trough 29. The sleeve 33 also has a flange 36, which abuts against recess 31 when the sleeve 33 and the collar component 27 are snap-fitted together.

As described above, the impaction plate 9 is disposed between body 2 and cup engaging element (3, 4). In order to facilitate this, the impaction plate 9 comprises a central aperture 37, which facilitates the mounting of impaction plate 9 on sleeve 33. The impaction plate 9 is mounted on the sleeve 33 in an axially movable manner, as described further below. An outer end 38 of the sleeve 33 comprises an annular trough 39, in which is mounted a split ring 40. This retains the impaction plate 9 on the sleeve 33.

Figure 8:
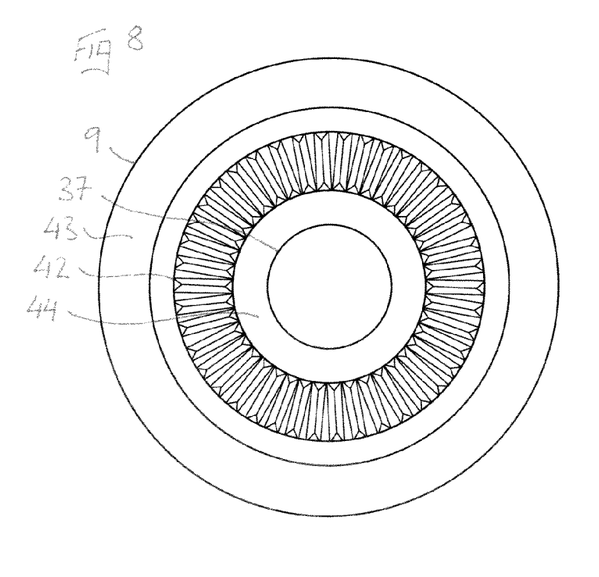
FIG. 8 is a rear view of an impaction plate forming a part of the prosthetic acetabular cup inserter and impactor as shown in FIG. 1.

Referring back to FIG. 1, a locking element is provided between body 2 and cup engaging element (3, 4), which comprise annular co-operating sets of teeth 41 and 42 provided at front face 32 of collar component 27, and at a rear face 43 of impaction plate 9. The teeth 41 are most clearly visible in FIG. 6, and the teeth 42 are visible in FIG. 8.

The rear face 43 of the impaction plate 9 is provided with an annular recess 44, and a coil spring 45 is mounted in compression between recess 44 and flange 36 of sleeve 33. The spring 45 urges the impaction plate 9 against the split ring 40, and therefore disengages teeth 41 and 42. As described further below, the action which serves to move the cone element 4 towards the impaction plate 9 to outwardly bias the resilient ring 3 and engage the cup 7, initially serves to axially move the impaction plate 9 on the sleeve 33, against the force of the spring 45, and therefore first engage teeth 41 and 42.

Figure 6:
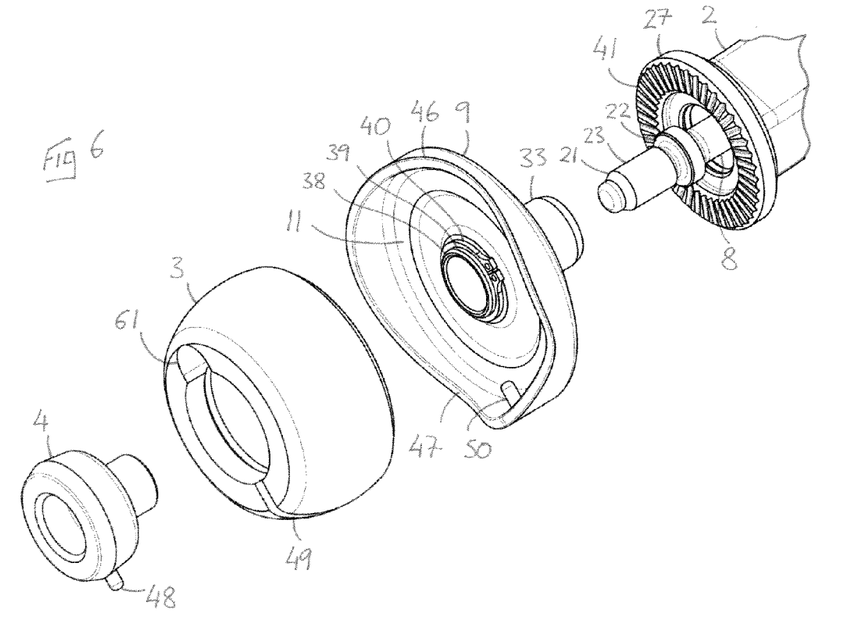
FIG. 6 is an exploded perspective view the portion of the prosthetic acetabular cup inserter and impactor as shown in FIG. 1.

Referring now to FIG. 6, the front face 11 of the impaction plate 9 has an annular cup engaging wall 46. As is clear from FIG. 6, the wall 46 comprises an irregular upper surface 47, comprising a plurality of convex portions. This shape is specifically adapted to correspond to that of the rim 10 of cup 7, which is shaped to mimic the contours of the natural shape of an acetabulum. Therefore, the rim 10 of cup 7 must be rotationally aligned with the upper surface 47 of wall 46 to rest properly thereon.

Figure 7:
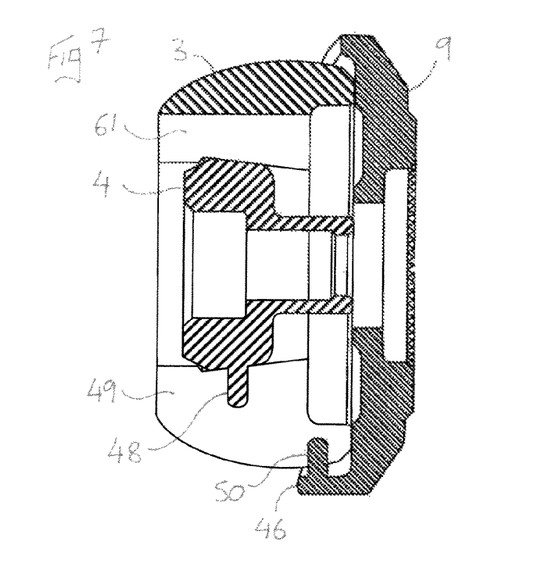
FIG. 7 is a cross-sectional side view of components of the prosthetic acetabular cup inserter and impactor as shown in FIG. 1.

The linkage between the drive train 8 and the impaction plate 9 comprises a first radially outwardly extending spigot 48 provided on cone element 4, which rotationally engages a radially extending slot 49 provided in resilient ring 3 at a first position, which is approximately a third of the way down, and a second radially inwardly extending spigot 50 provided on cup engaging wall 46, which rotationally engages slot 49 at a second position, which is about a fifth of the way up. This is most clearly illustrated in FIG. 7, which is a cross-sectional view through the ring 3, the cone element 4 and the impaction plate 9, along a plane passing through the middle of the slot 49. Therefore, rotation of the cone element 4 by the rod 21 is transmitted to the impaction plate 9 via the ring 3.

Figures 3, 4:
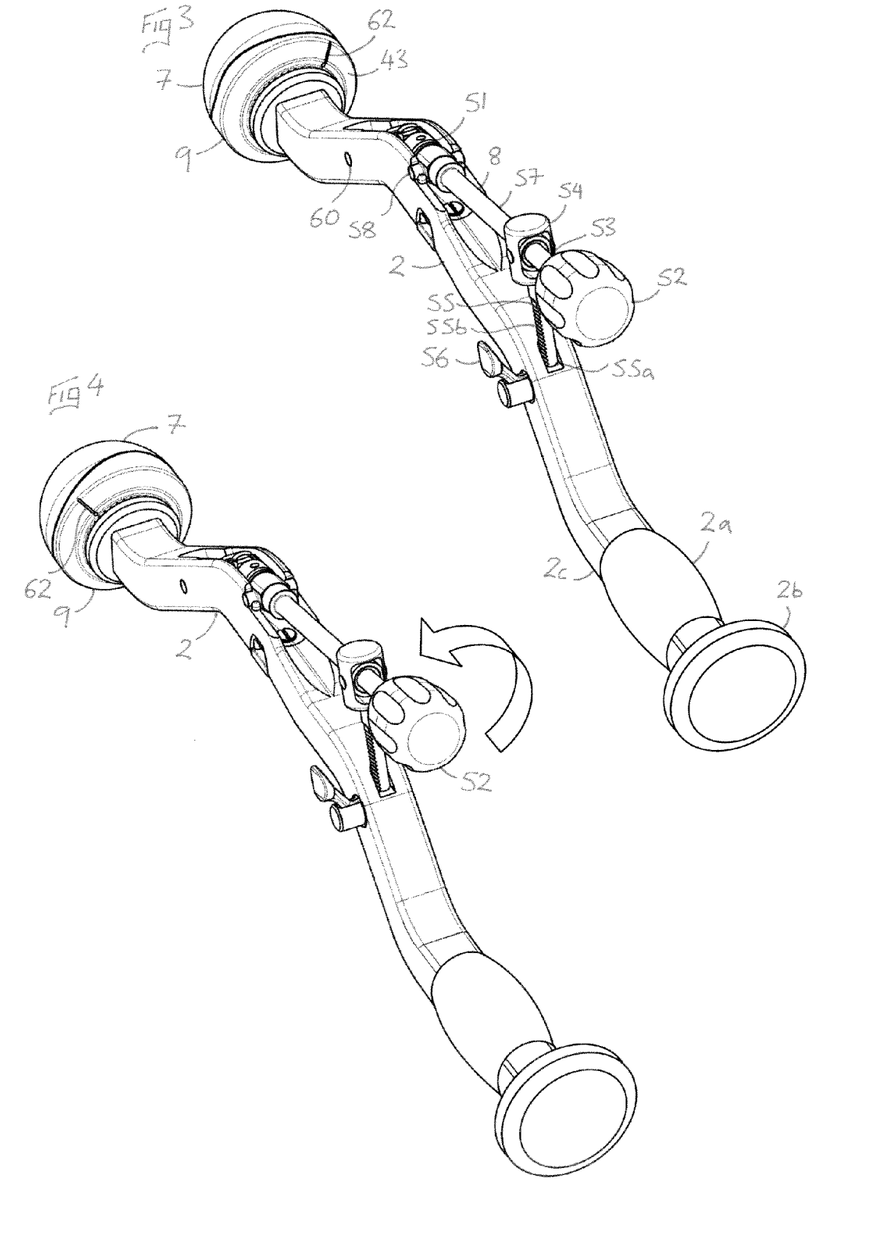
FIG. 3 is a perspective view of the prosthetic acetabular cup inserter and impactor as shown in FIG. 1, in the second in use configuration.
FIG. 4 is a perspective view of the prosthetic acetabular cup inserter and impactor as shown in FIG. 1, in a third in use configuration.

Referring to FIG. 3, it can be seen that the body 2 is curved, in the known way which is suitable for MIS. The body 2 had a handle 2a and an impaction anvil 2b at a second end 2c thereof. The handle 2a facilitates the manipulation of the body 2 in use, and the impaction anvil 2b allows for an impaction force to be imparted to the cup 7 to fit it in the acetabulum in use. The longitudinal axes of the cup engaging element (3, 4) and handle 2a are aligned so the impaction force is applied to the cup in a linear fashion. Such a configuration is known, and is not further described here.

As is also clear from FIG. 3, the rigid drive train 8 is carried by the body 2, and emerges therefrom at an intermediary opening 51. An operating knob 52 is provided at a second end 53 of the drive train 8. Axial rotation of the operating knob 52 is transmitted to the cone element 4 via axial rotation of the rods 19 and universal joints 20 of the drive train 8.

The second end 53 of the drive train 8 is supported by an adjustable housing 54, mounted on the end of a rack 55. The rack 55 is disposed in a slot 55a in the body 2, and is moveable therethrough both towards and away from the body 2. The position of the rack 55 is determined by a spring loaded ratchet (not visible) which is disposed inside the body 2, and which extends laterally into slot 55a to engage the toothed surface 55b of the rack 55 and hold it in position. In an engaged position the ratchet is configured to allow the rack 55 to ride over it when it is moved towards the body 2, but to prevent the rack 55 from moving away from the body 2. In a disengaged position the ratchet allows the rack 55 to move freely in the slot 55a. Engagement and disengagement of the ratchet is controlled by lever 56. In the position shown in FIGS. 3 and 4 the ratchet is in the engaged position, and movement of the lever 56 away from the body 2 disengages the ratchet.

Movement of the rack 55 and the housing 54 towards the body 2 rotates outer end rod 57 lengthwise about first pivot mounting 58. (The first pivot mounting 58 axially rotationally supports the outer end rod 57, and does not axially rotate when the knob 52 is axially rotated in use.) Outer end rod 57 is connected to intermediary rod 59 (visible in FIG. 1) beyond first pivot mounting 58, and therefore lengthwise rotation of outer end rod 57 about first pivot mounting 58 rotates intermediary rod 59 lengthwise about its own second pivot mounting 60. (Again, the second pivot mounting 60 axially rotationally supports the intermediary rod 59, and it does not axially rotate when the knob 52 is axially rotated in use.) Intermediary rod 59 is connected to inner end rod 21 (again visible in FIG. 1) beyond the pivot mounting 60, and therefore lengthwise rotation of the intermediary rod 59 about pivot mounting 60 axially moves the inner end rod 21 through sleeve 33. Initially this moves the impaction plate 9, via the cone element 4 and the ring 3, towards the front face 32 of the collar component 27, so the teeth 41 and 42 are engaged to secure the impaction plate 9 against rotation. This initial movement is against the force of the spring 45. Once the impaction plate 9 abuts against the collar component 27 further movement of the inner end rod 21 through sleeve 33 draws the cone element 4 towards the impaction plate 9, which serves to radially outwardly bias and/or expand the ring 3 to engage the cup 7.

Movement of the rack 55 and the housing 54 away from the body 2 achieves the opposite result. Although in fact, when the ratchet is disengaged the ring 3 is released from its outwardly biased state, and it contracts back to its neutral state, pushing the cone 4 back out, which in turn acts to move the drive train 8 in the opposite manner to as described above, forcing the rack 55, housing 54 and operating knob 52 to move away from the body 2. Once this has happened the spring 45 is released from its compressed state, and it is free to expand and disengage the teeth 41 and 42.

It will be appreciated that the lengthwise rotation of intermediary rod 59 is not transmitted into a perfectly linear axial movement of inner end rod 21, because the universal joint 20 therebetween follows an orbital path about pivot mounting 60. However, the required axial movement of the inner end rod 21 is short, and any deviation caused by the orbital movement of the universal joint 20 is well within functional tolerances.

The ring 3 has an axially extending cut-out 61 to increase flexibility, which facilitates its radial biasing and/or expansion in use.

In use the inserter and impactor operates as follows. Prior to engagement with the cup 7, the cone element 4 is arranged in the preliminary position and the teeth 41, 42 in the unlocked position. This is achieved by placing the ratchet in its disengaged position, so the ring 3 is not outwardly biased and holds the cone element 4 at an outer end of the first portion 13 of the central aperture 12, and so the spring 45 is free to push the impaction plate 9 away from the collar component 27. The ratchet is then engaged by movement of the lever 56 towards the body 2, so that the operating knob 52 will be held in position when later moved towards the body 2 as described below.

As shown in FIG. 1, the surgeon then introduces a cup 7 to the ring 3. In the preliminary position as shown, the cup 7 can be forced onto the ring 3 and held in place as shown in FIG. 2. As such, the cup 7 is partially engaged on the ring 3, as it can be manually removed fairly easily if required. During this mounting process the second portion 14 of the aperture 12 may engage the second portion 16 of the cone element 4 to prevent significant axial compression of the resilient ring 3.

The cup 7 is aligned with the cup engaging wall 46 such that the irregular shapes of the upper surface 47 of the wall 46 and the rim 10 of the cup 7 fit together.

The surgeon then axially rotates the knob 52 to align the cup 7 as desired in relation to the body 2. This is illustrated by FIGS. 3 and 4. A visual marker 62 is provided on the rear face 43 of the impaction plate 9, and in FIG. 3 the marker 62 is at approximately 45 degrees to a plane through which the body 2 passes. If the operating knob 52 is axially rotated as illustrated by the arrow in FIG. 4, the cup engaging element (3, 4), the impaction plate 9 and the cup 7 are all rotated through approximately 90 degrees in an anti-clockwise direction, by virtue of the axial rotation of the rigid drive train 8 being transmitted to the cone element 4, which then imparts this movement to the ring 3 via spigot 48, which then in turn imparts this movement to the impaction plate 9 via slot 49.

The marker 62 gives the surgeon a visual indication of the degree of the axial rotation performed. The marker 62 is aligned with a particular portion of the cup engaging wall 46, and therefore with a particular portion of the rim 10 of the cup 7. Therefore, the surgeon can orient the cup 7 as desired in relation to the body 2, so the cup 7 can be placed correctly in the acetabulum with the body 2 oriented as efficiently as possible in relation to the insertion into the patient.

During this process the spring 45 holds the impaction plate 9 away from the collar component 27, so the teeth 41 and 42 are held in the unlocked position. This removes any requirement for the surgeon to hold the cup engaging element (3, 4) in the unlocked position, which makes the axial rotation process easier.

Figure 5:
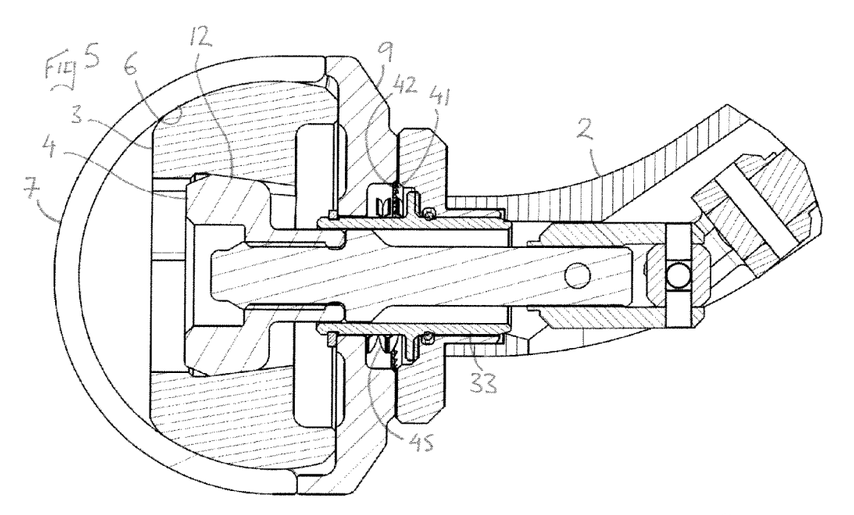
FIG. 5 is a cross-sectional side view of the portion of the prosthetic acetabular cup inserter and impactor as shown in FIG. 1, in a fourth in use configuration.

Once the desired relative rotational position between the cup 7 and the body 2 is achieved, the surgeon then pushes the operating knob 52 downward towards the body 2, rotating the outer end rod 57 lengthwise about the pivot mounting 58. As described above, this lengthwise rotational movement of the outer end rod 57 is transmitted to the cone element 4 via the lengthwise rotational movement of the intermediary rod 59 and the axial movement of the inner end rod 21. Initially this brings the impaction plate 9 into engagement with the collar component 27 against the force of the spring 45, so the teeth 41, 42 mesh in a locked position. Then, the cone element 4 is axially moved a short distance towards the impaction plate 9, to the position illustrated in FIG. 5.

In this engaged position the ring 3 is radially outwardly biased, and is forced intro greater contact with the interior surface 6 of the cup 7, by virtue of the relative movement of the tapered cone element 4 inside the tapered central aperture 12. This radial biasing compresses the ring 3 against the interior surface 6 of the cup 7, firmly fixing the cup 7 in a fully engaged position. In contrast to the partially engaged position shown in FIG. 2, the cup 7 cannot be readily manually removed from the ring 3.

Therefore, with one short downward movement of the operating knob 52 the cup 7 is fully engaged on the ring 3, and locked against any further rotation in relation to the body 2.

Downward movement of the operating knob 52 towards the body 2 forces the rack 55 to ride over the ratchet until the engaged position is achieved, and then the ratchet locks the cone element 4 and the teeth 41, 42 in position.

It should be noted that the rotational transmission arrangement of the spigot 48 in the slot 49 is such that there is free axial movement of the cone element 4 in relation to the ring 3. Therefore, this simple configuration of radial linkage does not interfere with the separate axial movement of the cone element 4 described above.

Now the cup 7 is fully engaged and rotationally locked in position, the surgeon can introduce the inserter and impactor 1 into the patient and place the cup 7 in the acetabulum. They can then use a hammer or similar tool to impart an impaction force to the anvil (not shown) at the second end of the body 2, which acts to firmly locate the cup 7 in the acetabulum.

It is theoretically possible for the surgeon to release the lever 56 so the rack 55 is disengaged, and the spring 45 can act to disengage the teeth 41, 42, while the inserter and impactor 1 is inside the patient. This would allow the surgeon to adjust the alignment of the cup 7 in relation to the body 2 during surgery, before locking it in another position. This could be done prior to insertion of the cup 7 into the acetabulum, or afterwards. However, it is not envisaged that this would be a normal manner of use, it is merely a possibility if required.

To release the cup 7 from the inserter and impactor 1 the lever 56 is moved away from the body 2 so the rack 55 is disengaged. The ring 3 is then released from its outwardly biased state, contracts and returns to the cone 4 to the preliminary position. In this state the ring 3 can be readily manually removed from the cup 7. Disengagement of the rack 55 also allows the spring 45 to expand and disengage the teeth 41 and 42. This may or may not be of any particular benefit to the surgeon in removing the inserter and impactor 1 from the patient.

After surgery the inserter and impactor 1 can be dismantled for cleaning. The ring 3 can be pulled from the cone element 4 by virtue of its resilience. The cone element 4 can then be unscrewed from the inner end rod 21 and removed therefrom. The split ring 40 can be removed from the sleeve 33 to allow the impaction plate 9 to be freed, before the sleeve 33 can be pulled from the collar component 27 against the force of the snap-fitting between those components. The rigid drive train 8 can also be dismantled to its component parts and removed from the body 2.

Figure 9:
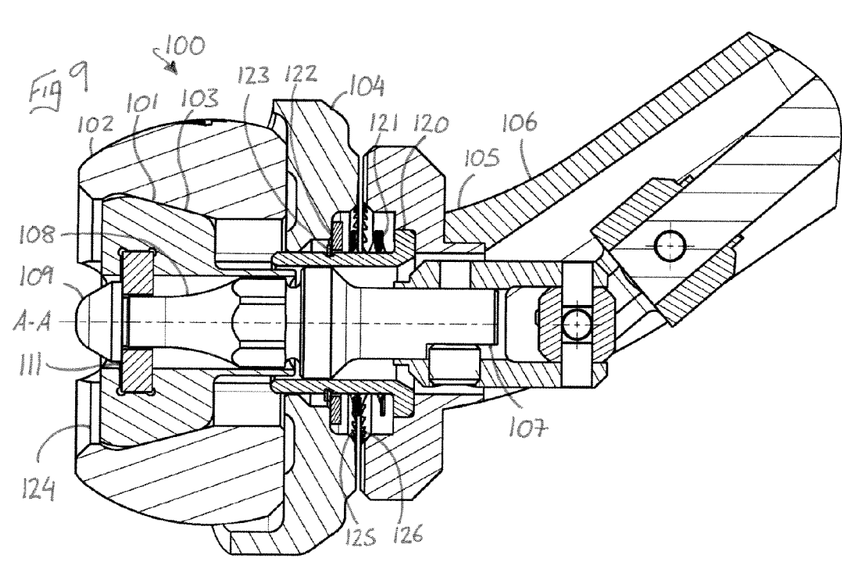
FIG. 9 is a cross-sectional side view of a portion of a second prosthetic acetabular cup inserter and impactor according to the present invention.

FIG. 9 shows a second inserter and impactor 100 which functions to engage and disengage a cup 7 in the same manner as inserter and impactor 1 described above, however it has a different construction. Firstly, the central aperture 101 of the resilient ring 102 comprises a taper angle which is greater than that of ring 3 described above. In particular the taper angle is 15 degrees in relation to an axis A-A of the ring 102, whereas the taper angle of ring 3 is 8 degrees. It has been found that a taper angle of 15 degrees improves the efficiency of the biasing action, and therefore the connection between the ring 102 and a cup in the fully engaged position.

Secondly, a single quick release mechanism is provided to secure the cone element 103, the resilient ring 102 and the impaction plate 104 to the first end 105 of the body 106. This replaces the arrangement of a screw thread between the cone element 4 and the inner end rod 21, and the split ring 40 retaining the impaction plate 9 used in inserter and impactor 1 described above.

Figure 10:
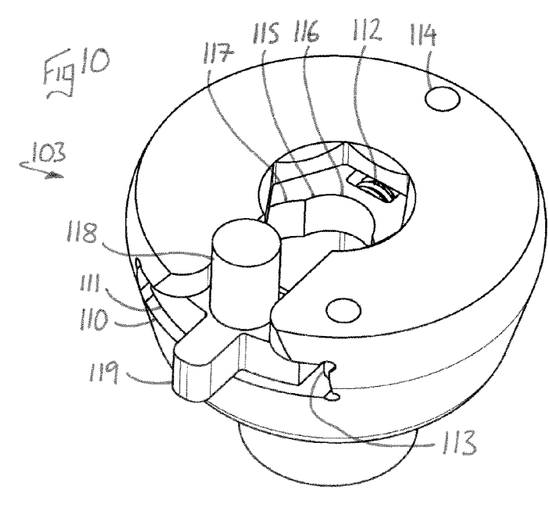
FIG. 10 is a perspective view of a cone element component of the second prosthetic acetabular cup inserter and impactor as shown in FIG. 9.

In particular, the inner end rod 107 comprises a tapering neck 108, and a head 109. Referring to FIG. 10, the cone element 103 comprises a laterally extending slot 110, in which is disposed a sliding lock member 111. A coil spring 112 is disposed in the slot 110 between the cone element 103 and the lock member 111, which biases the lock member out of the slot 110. A pin 113 extends axially into the slot 110 from above, which abuts against a shoulder (not visible) of the lock member 111 and serves to retain it in the slot 110, against the force of the spring 112. A further pin 114 also extends axially into the slot 110 from above, and serve to retain the spring 112 therein, so it cannot escape. Therefore, the lock member 111 is slideable laterally in the slot 110 against the force of the spring 112. It can be moved between a lock position as shown in FIG. 10 in which the spring 112 holds it against the pin 113, and a release position in which it is moved laterally inwardly a short distance.

The lock member 111 comprises a shaped aperture 115 with a first annular section 116 and a second annular section 117 larger in diameter than the first 116. In the lock position shown in FIG. 10 the first annular section 116 is axially aligned with an axis (A-A) of the cone element 103, and in the release position the second annular section 117 is axially aligned with said axis (A-A). The first annular section 116 is shaped to engage the neck 108 of the inner end rod 107, and is smaller in diameter than the head 109 thereof, while the second annular section 117 has a diameter which is greater than that of the head 109.

The lock member 111 also comprises a trigger 118, as well as a spigot 119 which rotationally engages a radially extending slot (not visible) provided in the resilient ring 103. This spigot 119 performs the same function as the spigot 48 formed in the side of the cone element 4 in inserter and impactor 1 described above.

Referring back to FIG. 9, the impaction plate 104 is freely axially disposed on sleeve 120, as opposed to being fixed thereon with a split ring, as in inserter and impactor 1 described above. In addition, sleeve 120 is welded in place and is not removable like sleeve 33. Further, coil spring 121 now acts against an annular plate 122 mounted on the sleeve 120, which is retained thereon by a retention ring 123. As such, the sleeve 120, the spring 121 and the plate 122 cannot be removed to form the first end 105 of the body 106.

As is also clear from FIG. 9, the resilient ring 102 comprises a lip 124, which serves to releasably retain the cone element 103 inside the aperture 101, so once connected together these two components will not inadvertently come apart.

Therefore, to construct the inserter and impactor 100, first the impaction plate 104 is mounted on the sleeve 120, so it abuts against the plate 122 as shown in FIG. 9. Next, the cone element 103 is mounted inside the resilient ring 102, and these two components are aligned with the axis A-A and introduced to the inner end rod 107. In order to releasably retain the cone element 103 on the inner end rod 107, the trigger 118 is moved laterally to slide the lock member 111 from the lock position as shown in FIG. 10 to the release position. As such, the second annular section 117 of the aperture 115 is aligned with the head 109, and the lock member 111 can pass thereover. The trigger 118 is then released, and the first annular section 116 moves into axial alignment with the neck 108 of the inner end rod 107, as shown in FIG. 9. As the first annular section 116 has a smaller diameter than the head 109, and as the spring 112 biases the lock member 111 into the lock position, the cone element 103 is locked in place on the inner end rod 107.

As is clear from FIG. 9, the coil spring 121 biases the plate 122 against the impaction plate 104, which in turn biases the resilient ring 102 and the cone element 103 away from the first end 105 of the body 106, pushing the lock member 111 into engagement with the head 109. In this position the teeth 125 and 126 are in the unlocked position, and the cone element 103, resilient ring 102 and impaction plate 104 can be axially rotated, as described above. The same mechanism as in inserter and impactor 1 described above is provided to rotate these components, and to move them into the locked position. However, the axial movement of the inner end rod 107 is transmitted to the cone element 102 via the head 109, which acts against the lock member 111.

To dismantle the inserter and impactor 100 after use a reverse of the above procedure is performed. The trigger 118 is moved laterally to slide the lock member 111 from the lock position as shown in FIG. 10 to the release position. This brings the second annular section 117 of the aperture 115 into axial alignment with the head 109, and the lock member 111 can pass thereover. The cone element 103 and resilient ring 102 are then freed as one unit, and the impaction plate 104 can also be removed from the sleeve 120. The spring 121 is retained, preventing it from inadvertently escaping. Therefore, with one simple action the quick release mechanism allows for the dismantling of the inserter and impactor 1 into a small number of easy to handle parts.

One further difference between the inserter and impactor 100 and inserter and impactor 1 described above is that the curvature of the body 106 begins closer to the first end 105, which shortens the whole device and makes it easier to insert into a patient in use.

The above described embodiment can be altered without departing from the scope of the invention. For example, in one alternative embodiment (not shown) the linkage means between the operating means and the impaction plate can be a direct connection between those components. A spigot can extend from an inner end rod of the drive train and engage a slot provided on the impaction plate.

In another alternative embodiment (not shown), the resilient ring is a snap-fit onto the front face of the impaction plate. The ring can be slightly larger than the inner diameter of the cup engaging wall, so it is retained within it.

In yet another alternative embodiment (not shown) the cup engaging element are any of the known constructions, including a screw thread fixing, or by means of other known compressible or expandable resilient ring configurations.

Thus, the present invention provides an inserter and impactor with the advantageous relative rotation between the cup engaging means and the body, which can be used with cups with an irregular outer peripheral rim portion acted upon in use by a correspondingly shaped impaction plate, because the impaction plate can also be rotated.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic acetabular cup inserter and impactor comprising a body, an expandable part-spherical cup engaging means disposed at a first end of said body and adapted to engage an inner surface of a cup with which it is used when expanded, and operating means adapted to axially rotate said cup engaging means in relation to said body in use, in which an impaction plate adapted to engage a rim of said cup is disposed between said body and said cup engaging means, and in which said impaction plate is connected to said operating means by linkage means which act to axially rotate said impaction plate in unison with said cup engaging means in use;

the operating means including an axially extending rod mounted within the cup engaging means moveable in an axial direction by the linkage means to expand the expandable cup engaging means; and a release element slidably mounted on the expandable cup engaging means moveable in a direction transverse to the axis of the rod for connecting the cup engaging means to the rod in a first position of the release element and releasing the cup engaging element from the rod in a second position.

2. The prosthetic acetabular cup inserter and impactor as claimed in claim 1 in which said linkage means comprises an axial rotational connection between said cup engaging means and said impaction plate.

3. The prosthetic acetabular cup inserter and impactor as claimed in claim 2 in which said cup engaging means comprises a cup engaging element adapted to engage an inner surface of said cup via outward biasing thereof, and biasing means adapted to bias said engaging element outwardly via relative axial movement therewith.

4. The prosthetic acetabular cup inserter and impactor as claimed in claim 3 in which said operating means is adapted to axially move said biasing means from a preliminary position in which said cup is partially engaged with said cup engaging element, into an engaged position in which said cup is fully engaged with said cup engaging element.

5. The prosthetic acetabular cup inserter and impactor as claimed in claim 4 in which locking means are provided between said body and said cup engaging means which are movable between a locked position in which said cup engaging means are locked against rotation in relation to said body, and an unlocked position in which said cup engaging means is rotatable in relation to said body.

6. The prosthetic acetabular cup inserter and impactor as claimed in claim 5 in which the operation of the operating means which serves to move said biasing means into said engaged position also serves to move said locking means into said locked position, and in which an operation of the operating means which serves to allow for said biasing means to move into said preliminary position also serves to allow for said locking means to move into said unlocked position.

7. The prosthetic acetabular cup inserter and impactor as claimed in claim 6 in which said locking means is spring loaded into said unlocked position.

8. The prosthetic acetabular cup inserter and impactor as claimed in claim 7 in which said locking means comprises co-operating sets of teeth provided at said first end of said body and at a rear face of said impaction plate.

9. The prosthetic acetabular cup inserter and impactor as claimed in claim 4 in which said impaction plate comprises a front face with an annular cup engaging wall, in which said cup engaging element abuts against said front face, and in which said biasing means moves towards said front face when it is moved into said engaged position.

10. The prosthetic acetabular cup inserter and impactor as claimed in claim 9 in which said cup engaging element comprises a resilient ring comprising a central aperture which tapers in a direction toward said front face, and in which said biasing means comprises a cone element disposed within said aperture and which comprises a taper corresponding with that of said aperture.

11. The prosthetic acetabular cup inserter and impactor as claimed in claim 10 in which said axial rotational connection between said cup engaging means and said impaction plate comprises a first radially outwardly extending spigot provided on said cone element which axially rotationally engages a radially extending slot provided in said resilient ring at a first position, and a second radially inwardly extending spigot provided on said cup engaging wall which axially rotationally engages said radially extending slot at a second position.

12. The prosthetic acetabular cup inserter and impactor as claimed in claim 4 in which said operating means comprises a rigid drive train carried by said body and comprising a connection to said biasing means at a first end thereof, and an operating knob at a second end thereof, which operating knob is axially rotatable to axially rotate said biasing means in relation to said body, and separately operable to axially move said biasing means into said engaged position.

13. The prosthetic acetabular cup inserter and impactor as claimed in claim 12 in which said second end of said rigid drive train is carried on a rack, in which said rack is disposed in a slot in said body, and is moveable therethrough both towards and away from said body, in which the position of said rack is determined by a spring loaded ratchet disposed inside said body, and which extends laterally into said slot to engage said rack, in which said ratchet is movable between an engaged position and a disengaged position, in which in said engaged position said ratchet allows said rack to ride over it when said rack is moved towards said body and prevents said rack from moving away from said body, in which in said disengaged position said ratchet allows said rack to move freely in said slot, in which movement of said second end of said rigid drive train towards said body is converted by the rigid drive train into axial movement of said biasing means into said engaged position.

14. The prosthetic acetabular cup inserter and impactor as claimed in claim 13 in which said rigid drive train comprises an outer end rod, an intermediary rod and an inner end rod, connected together end to end in sequence by universal joints, in which said outer end rod is mounted part way along its length in a first pivot mounting, in which said intermediary rod is mounted part way along its length in a second pivot mounting, in which said inner rod is mounted for axial movement in a sleeve mounted at a first end of said body, in which movement of said second end of said rigid drive train towards said body rotates said outer end rod lengthwise about said first pivot mounting in a first direction, which rotates said intermediary rod lengthwise about said second pivot mounting in a second direction, which moves said inner rod substantially axially through said sleeve.

15. The prosthetic acetabular cup inserter and impactor as claimed in claim 12 in which said biasing means is releasably fixed to said first end of said drive train with a spring loaded quick release mechanism.

16. The prosthetic acetabular cup inserter and impactor as claimed in claim 8 in which a sleeve is disposed between a first end of said body and said impaction plate, in which said impaction plate comprises a central aperture through which said sleeve passes, in which said impaction plate is axially moveable on said sleeve between the locked and unlocked positions of said locking means, and in which a second end of said sleeve is snap-fitted to said first end of said body.

17. The prosthetic acetabular cup inserter and impactor as claimed in claim 1 in which said impaction plate is mounted to said first end of said body with a spring loaded quick release mechanism.

18. The prosthetic acetabular cup inserter and impactor as claimed in claim 9 in which said cup engaging element is a snap-fit onto said front face.

19. The prosthetic acetabular cup inserter and impactor as claimed in claim 1 in which a second end of said body is provided with a handle and an impaction anvil or plate.

20. The prosthetic acetabular cup inserter and impactor as claimed in claim 19 in which said body is curved.

21. The prosthetic acetabular cup inserter and impactor as claimed in claim 20 in which longitudinal axes of said cup engaging means and said handle are substantially aligned.

22. The prosthetic acetabular cup inserter and impactor as claimed in claim 9 in which said annular cup engaging wall comprises an irregular upper surface comprising a plurality of convex portions.

23. A prosthetic acetabular cup inserter and impactor comprising a body, a cup engaging means disposed at a first end of said body and adapted to engage an inner surface of a cup with which it is used, and operating means adapted to axially rotate said cup engaging means in relation to said body in use, in which an impaction plate adapted to engage a rim of said cup is disposed between said body and said cup engaging means, and in which said impaction plate is connected to said operating means by linkage means which act to axially rotate said impaction plate in unison with said cup engaging means in use;

wherein said linkage means comprises an axial rotational connection between said cup engaging means and said impaction plate and in which said cup engaging means comprises a cup engaging element adapted to engage an inner surface of said cup via outward biasing thereof, and biasing means adapted to bias said engaging element outwardly via relative axial movement therewith, and in which said operating means is adapted to axially move said biasing means from a preliminary position in which said cup is partially engaged with said cup engaging element, into an engaged position in which said cup is fully engaged with said cup engaging element;

wherein said operating means comprises a rigid drive train carried by said body and comprising a connection to said biasing means at a first end thereof, and an operating knob at a second end thereof, which operating knob is axially rotatable to axially rotate said biasing means in relation to said body, and separately operable to axially move said biasing means into said engaged position;

wherein said second end of said rigid drive train is carried on a rack, in which said rack is disposed in a slot in said body, and is moveable therethrough both towards and away from said body, in which the position of said rack is determined by a spring loaded ratchet disposed inside said body, and which extends laterally into said slot to engage said rack, in which said ratchet is movable between an engaged position and a disengaged position, in which in said engaged position said ratchet allows said rack to ride over it when said rack is moved towards said body and prevents said rack from moving away from said body, in which in said disengaged position said ratchet allows said rack to move freely in said slot, in which movement of said second end of said rigid drive train towards said body is converted by the rigid drive train into axial movement of said biasing means into said engaged position; and wherein said rigid drive train comprises an outer end rod, an intermediary rod and an inner end rod, connected together end to end in sequence by universal joints, in which said outer end rod is mounted part way along its length in a first pivot mounting, in which said intermediary rod is mounted part way along its length in a second pivot mounting, in which said inner rod is mounted for axial movement in a sleeve mounted at a first end of said body, in which movement of said second end of said rigid drive train towards said body rotates said outer end rod lengthwise about said first pivot mounting in a first direction, which rotates said intermediary rod lengthwise about said second pivot mounting in a second direction, which moves said inner rod substantially axially through said sleeve.

24. A prosthetic acetabular cup inserter and impactor comprising a body, a cup engaging means disposed at a first end of said body and adapted to engage an inner surface of a cup with which it is used, and operating means adapted to axially rotate said cup engaging means in relation to said body in use, in which an impaction plate adapted to engage a rim of said cup is disposed between said body and said cup engaging means, and in which said impaction plate is connected to said operating means by linkage means which act to axially rotate said impaction plate in unison with said cup engaging means in use;
  wherein said linkage means comprises an axial rotational connection between said cup engaging means and said impaction plate;
  wherein said cup engaging means comprises a cup engaging element adapted to engage an inner surface of said cup via outward biasing thereof, and biasing means adapted to bias said engaging element outwardly via relative axial movement therewith;
  in which said operating means is adapted to axially move said biasing means from a preliminary position in which said cup is partially engaged with said cup engaging element, into an engaged position in which said cup is fully engaged with said cup engaging element;
  wherein locking means are provided between said body and said cup engaging means which are movable between a locked position in which said cup engaging means are locked against rotation in relation to said body, and an unlocked position in which said cup engaging means is rotatable in relation to said body;
  wherein the operation of the operating means which serves to move said biasing means into said engaged position also serves to move said locking means into said locked position, and in which an operation of the operating means which serves to allow for said biasing means to move into said preliminary position also serves to allow for said locking means to move into said unlocked position;
  wherein said locking means is spring loaded into said unlocked position;
  wherein said locking means comprises co-operating sets of teeth provided at said first end of said body and at a rear face of said impaction plate; and
  wherein a sleeve is disposed between a first end of said body and said impaction plate, in which said impaction plate comprises a central aperture through which said sleeve passes, in which said impaction plate is axially moveable on said sleeve between the locked and unlocked positions of said locking means, and in which a second end of said sleeve is snap-fitted to said first end of said body.

* * * * *